United States Patent [19]

Rae et al.

[11] Patent Number: 4,904,688
[45] Date of Patent: Feb. 27, 1990

[54] TRICYCLIC AMINE DERIVATIVES

[75] Inventors: Duncan R. Rae, Lanark; James Cairns, Cumbernauld, both of Scotland

[73] Assignee: Akzo N.V., Arnhem, Netherlands

[21] Appl. No.: 320,340

[22] Filed: Mar. 8, 1989

[30] Foreign Application Priority Data

Mar. 11, 1988 [EP] European Pat. Off. ......... 88302129.7

[51] Int. Cl.$^4$ .................. A61K 31/335; C07D 313/14
[52] U.S. Cl. ........................................ 514/450; 549/9; 549/354; 540/479; 546/196; 546/202; 546/203; 546/204; 548/525; 548/529; 564/427; 514/183; 514/431; 514/422; 514/428; 514/429; 514/320; 514/324; 514/325; 514/656

[58] Field of Search .................. 549/354, 9; 540/479; 514/183, 431, 450, 320, 324, 325, 656, 422, 428, 429; 546/196, 202, 203, 204; 548/525, 529

[56] References Cited

U.S. PATENT DOCUMENTS

| 4,100,173 | 7/1978 | Gerecke et al. | 549/354 |
| 4,496,557 | 1/1985 | Malen et al. | 514/320 |
| 4,837,227 | 6/1989 | Ong et al. | 514/450 |

*Primary Examiner*—Glennon H. Hollrah
*Assistant Examiner*—Mark W. Russell
*Attorney, Agent, or Firm*—William M. Blackstone

[57] ABSTRACT

The present invention deals with dibenzo-oxocin-, dibenzo-thiocin-, dibenzo-azocin- and dibenzocyclo-octenamine derivatives suitable for use as antipsychotic compounds without extra-pyrimidal side-effects.

6 Claims, No Drawings

TRICYCLIC AMINE DERIVATIVES

The present invention deals with tricyclic amine derivatives. More particularly the invention refers to dibenzo-oxocin-, dibenzo-thiocin-, dibenzo-azocin- and dibenzocyclo-octen-amine derivatives of the general formula

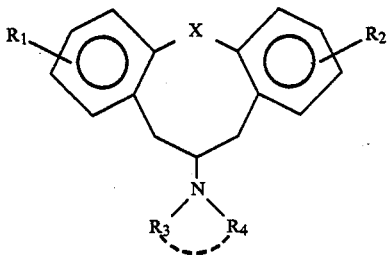

I and pharmaceutically acceptable salts thereof, wherein
X represents oxygen, sulphur, >NR or —CH₂—;
R is hydrogen or alkyl (1–4 C);
R₁ and R₂ represent one, two, three or four substituents at the benzo moiety selected from hydrogen, hydroxy, alkyl (1–6C), alkoxy (1–6C), halogen, CF₃ or CN;
R₃ and R₄ represent hydrogen or alkyl (1–6C) or;
R₃ and R₄ together with the nitrogen atom to which they are attached form a heterocyclic 5 or 6-membered ring.

The invention also refers to methods for the preparation of the above compounds and to pharmaceutical preparations containing same.

The compounds of formula I have very potent antidopamine and anti-5HT₂ activities, which render them extremely suitable for use as antipsychotic compounds without extra-pyrimidal side-effects.

The compounds of the invention can be prepared by conventional chemical methods known for the preparation of analogous compounds.

A simple and direct method of preparing the compounds of formula I consists of a reductive amination of a starting ketone of the formula II,

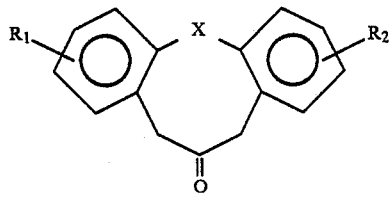

II in which R₁, R₂ and X have the meanings assigned above, with an amine of the formula III,

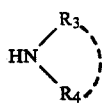

III in which R₃ and R₄ have the meanings assigned above in the presence of or followed by a treatment with a reducing agent, such as formic acid, a metalhydride e.g. LiAlH₄, NaBH₄, Na(CN)BH₃ etc, or hydrogen/-catalyst.

A very convenient synthesis of compounds of formula I in which R₃ and R₄ are either both hydrogen or methyl or R₃ is methyl and R₄ is hydrogen consists of a reaction between a ketone of formula II with either formamide, N-methylformamide or N,N-dimethylformamide in the presence of formic acid, followed by hydrolysis or reduction of the formyl moiety when present as appropriate.

The key-intermediate of formula II can be prepared as indicated in the attached reaction scheme. The method indicated is described more in detail in the Examples.

The compounds of formula I may have (where R₁≠R₂) an asymmetric centre. As a result thereof a racemic mixture of formula I as well as separate optical isomers of formula I are possible. Both the racemic mixture as well as the separate optical isomers are numbered among the compounds of the invention.

The separate optical isomers may be prepared directly from optically active intermediates or may be obtained by a resolution of the racemic mixture e.g. in the usual manner with the acid of an optically active acid such as (+) or (−) tartaric acid.

Subsequent to the above mentioned reactions the unsubstituted or monosubstituted amines I (R₃ and/or R₄≠alkyl) may be alkylated in the usual manners for example by reaction with an alkylhalide, or by acylation followed by reduction of the carbonyl moiety. For the introduction of methyl groups at the nitrogen atom the procedure of Eschweiler-Clarke (formaldehyde/formic acid) or the reaction with formaldehyde and sodium cyanoborohydride in e.g. acetonitrile is preferred.

The preferred method yielding mono- or dimethyl substituted amine derivatives according to formula I consists of the reaction of the ketone of formula II with N-methyl-formamide in the presence of formic acid followed by either hydrolysis or reduction of the formyl group.

An alkyl group as meant in the definitions of R₁, R₂, R₃ and R₄ is a branched or unbranched alkyl group with 1–6 carbon atoms such as methyl, ethyl, propyl, isopropyl, butyl, isobutyl, tert.butyol, n.pentyl, isopentyl and hexyl. An alkyl group of 1–4C atoms is preferred.

The alkyl group in the alkoxy moiety has the same meaning.

The heterocyclic 5- or 6-membered ring in the definition of R₃ and R₄ may either be saturated or unsaturated, such as a pyrrolino group, a pyrrolidino group, a piperidino group, a morpholino group, a piperazino group, etc. The N-methylpiperazino group is to be preferred.

Amines according to the general formula III, which may be used in the aforesaid condensation reaction(s) to obtain the compounds of the invention, are, for example ammonia, methylamine, dimethylamine, diethylamine, isopropylamine, dibutylamine, t.butylamine, pyrroline, pyrrolidine, piperidine, morpholine, piperazine, N-methyl-piperazine, etc.

The novel compounds of formula I may be isolated from the reaction mixture in the form of a pharmaceutically acceptable salt, dependent on the conditions in which the reaction is carried out. The pharmaceutically acceptable salts may also be obtained by treating the free base I with an organic or inorganic acid such as HCl, HBr, HI, H₂SO₄, H₃PO₄, acetic acid, propionic acid, glycolic acid, maleic acid, fumaric acid, malonic acid, succinic acid, tartaric acid, citric acid, benzoic acid, ascorbic acid etc.

The compounds of the invention may be administered enterally or parenterally, preferably in a daily dosage of from 0,01–50 mg per kg bodyweight. More specifically a daily dose of 5–750 mg is preferred for the treatment of human beings.

Mixed with suitable auxiliaries the compounds I may be compressed into solid dosage units, such as pills, tablets and coated tablets or be processed into capsules.

By means of suitable liquids the compounds I can also be applied as an injection preparation in the form of solutions, suspensions or emulsions or in the form of a spray.

Preferred compounds according to the invention have the general formula I in which whether or not in combination:

(1) X is oxygen;
(2) the benzo-moieties are unsubstituted or mono- or disubstituted;
(3) the amino moiety is a mono- or dimethyl amino moiety.

Most preferred is the compound 3-chloro-6,7-dihydro-N-methyl-5H-dibenz[b,g]-oxocin-6-amine and pharmaceutically acceptable salts thereof.

ous tetrahydrofuran, then the mixture was filtered, and the residue was washed thoroughly with hot methylbenzene.

The filtrate was evaporated to dryness and the residue was triturated with 1,1'-oxybisethane. The resulting crystals of 10,11-dihydro-10-hydroxy-dibenz[b,f]oxepine-10-methanamine were filtered off and dried (42.3 g). The mother liquor was treated with gaseous hydrogen chloride, which precipitated the remainder of the product as its hydrochloride salt. After filtration, the salt was stirred in a mixture of dichloromethane and 50% aqueous potassium hydroxide solution. The organic phase was separated and washed several times with saturated sodium chloride solution, then dried over sodium sulphate, and evaporated to give a further quantity of the desired amine (4.3 g).

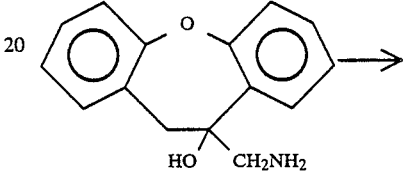

B.

REACTION SCHEME

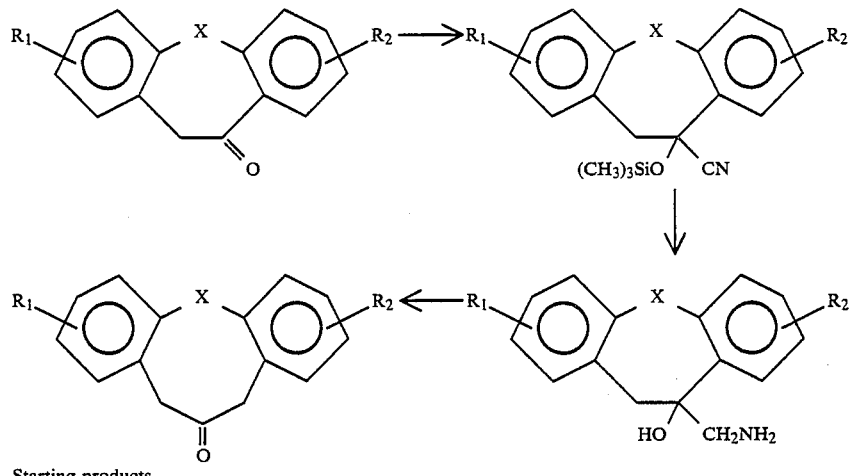

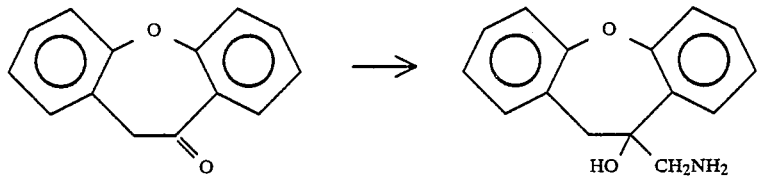

Starting products

A.

Trimethylsilanecarbonitrile (25 g) was added over several minutes to a mixture of dibenz[b,f]oxepin-10(11H)-one (50 g), Collect Czech. Chem. Commun. 34,2258,(1969), and KCN/18-crown-6 (1.25 g - a 1:1 molar homogeneous mixture of potassium cyanide and 1,4,7,10,13,16-hexaoxacyclooctadecane). The reaction mixture became warm and the solid material rapidly dissolved.

The solution was stirred for one hour at ambient temperature, then it was diluted with dry methylbenzene (100 ml) and added dropwise to a stirred suspension of lithium tetrahydroaluminate (13 g) in dry methylbenzene (150 ml) and dry 1,1'-oxybisethane (150 ml). When the addition had been completed, the mixture was refluxed for thirty minutes, then cooled. Excess reagent was destroyed by careful addition of 50% aque-

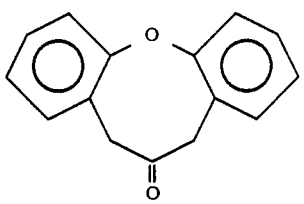

10,11-Dihydro-10-hydroxy-dibenz[b,f]oxepine-10-methanamine (46.6 g - as prepared in example A) was dissolved in a mixture of water (940 ml) and acetic acid (23 ml), and the solution was filtered and cooled below 5° C. To this cooled solution was quickly added a solution of sodium nitrite (20.5 g) in the minimum of water, the cooling was then removed, and the mixture was allowed to stand at ambient temperature for eighteen hours. The product was filtered, dissolved in dichloromethane, and the solution was filtered through silica, then evaporated. The residue was crystallised from 1,1'-oxybisethane/n-hexane to give pure 5H-dibenz[b,g]oxocin-6(7H)-one (34 g). M.P. 86° C. (Lit. 84.5° C. J.Org.Chem.34.1165(1969).

In a similar way, the following ring-expanded ketones were also prepared:
3-Chloro-5H-dibenz[b,g]oxocin-6(7H)-one. M.P. 84° C.
3-Methyl-5H-dibenz[b,g]oxocin-6(7H)-one M.P. 87.5° C.
1-Methyl-5H-dibenz[b,g]oxocin-6(7H)-one M.P. 104° C.
5H-Dibenz[b,g]thiocin-6(7H)-one M.P. 122.5° C.
N-Methyl-5H-dibenz[b,g]azocin-6(7H)-one M.P. 130° C.
7,12-Dihydro-dibenzo[a,d]cycloocten-6(5H)-one M.P. 151.5° C.
3,9-Chloro-5H-dibenz[b,g]oxocin-6(7H)-one M.P. 191° C.

EXAMPLE 1

6,7-Dihydro-N-methyl-5H-dibenz[b,g]oxocin-6-amine.HCl

5H-Dibenz[b,g]oxocin-6(7H)-one (3 g - as prepared in B) was dissolved in a mixture of formic acid (3 ml) and methylformamide (12 ml) containing magnesium chloride hexahydrate (0.6 g), and the solution was refluxed for three hours. The cooled reaction mixture was diluted with water and neutralised with sodium carbonate solution, then the product was extracted into 1,1'-oxybisethane. The extract was washed with water, sodium carbonate solution and water then dried over sodium sulphate, and evaporated to give 6,7-Dihydro-N-methyl-5H-dibenz[b,g]oxocine-6-formamide.

The crude product (3.5 g) was dissolved in ethanol (70 ml), and 50% aqueous potassium hydroxide (17.5 ml) was added and the mixture was refluxed for eighteen hours. After it had been evaporated to low volume, the mixture was diluted with water, and the product was extracted into 1,1'-oxybisethane. The extract was washed several times with water, and dried over sodium sulphate. Gaseous hydrogen chloride was passed into the solution and the precipitate was collected to give 6,7-Dihydro-N-methyl-5H-dibenz[b,g]oxocin-6-amine hydrochloride. M.P. 250° C.

In a similar way, the following methyl amines were also prepared;
3-Chloro-6,7-dihydro-N-methyl-5H-dibenz[b,g]oxocin-6-amine hydrochloride. M.P. 210° C.
6,7-Dihydro-N-methyl-5H-dibenzo[b,g]thiocin-6-amine hydrochloride. M.P. 240° C.
N-Methyl-5,6,7,12-tetrahydro-dibenz[a,d]cycloocten-6-amine hydrochloride. M.P. 232° C.
6,7-Dihydro-1,N-dimethyl-5H-dibenz[b,g]oxocin-6-aminehydrochloride. M.P. 284° C.
6,7-Dihydro-3,N-dimethyl-5H-dibenz[b,g]oxocin-6-amine hydrochloride. M.P. 182° C.
3,9-Dichloro-6,7-dihydro-N-methyl-5H-dibenz[b,g]oxocin-6-amine hydrochloride. M.P. 237° C.

EXAMPLE 2

6,7-Dihydro-N,N'-dimethyl-5H-dibenz[b,g]-azocin-6-amine. HCl

N-methyl-5H-dibenz[b,g]azocin-6(7H)-one (4 g) was suspended in a 33% solution of methylamine in ethanol. After sixty hours at room temperature, the resulting solution was treated with sodium tetrahydroborate (1 g) for half an hour. The reaction mixture was then dilute with water and the product was extracted into 1,1'-oxybisethane. Gaseous hydrogen chloride was passed into the solution and the precipitate was collected to give 6,7-dihydro-N,N'-dimethyl-5H-dibenz[b,g]azocin-6-amine hydrochloride. M.p. 195° C.

In a similar manner the following amines were prepared:
6,7-dihydro-N-methyl-5H-dibenz[b,g]oxocin-6-amine.HCl. M.P. 250° C.;
6,7-dihydro-N-methyl-5H-dibenz[b,g]thiocin-6-amine.HCl. M.P. 240° C.

EXAMPLE 3

6,7-Dihydro-N,N-dimethyl-5H-dibenz[b,g]oxocin-6-amine. HCl 6,7-Dihydro-N-methyl-5H-dibenz[b,g]oxocine-6-formamide, (3.4 g - as prepared in example 1) was dissolved in 1,1'-oxybisethane (34 ml), and the solution was added dropwise to a solution of lithium tetrahydro-aluminate (1.1 g) in 1,1'-oxybisethane (34 ml). After the addition had been completed, the mixture was refluxed for one hour, then cooled, and the excess reducing agent was destroyed by careful addition of 50% aqueous tetrahydrofuran.

The mixture was filtered, and the filtrate was evaporated to an oil which was dissolved in 1,1'-oxybisethane. Gaseous hydrogen chloride was passed into the solution to give a precipitate of the salt which was recrystallised from methanol/1,1'-oxybisethane to give 6,7-dihydro-N,N-dimethyl-5H-dibenz[b,g]oxocin-6-amine hydrochloride. M.P. 120° C.

In a similar way, the following dimethylamines were prepared:
3-Chloro-6,7-dihydro-N,N-dimethyl-5H-dibenz[b,g]oxocin-6 amine-(Z)-2-butendioate (1:1) salt. M.P. 154° C.
6,7-Dihydro-N,N-dimethyl-5H-dibenzo[b,g]thiocin-6-amine hydrochloride. M.P. 220° C.
N,N-Dimethyl-5,6,7,12-tetrahydro-dibenzo[a,d]cycloocten-6amine hydrochloride. M.P. 238° C.

EXAMPLE 4

6,7-Dihydro-5H-dibenz[b,g]oxocin-6-amine.HCl

5H-Dibenz[b,g]oxocin-6(7H)-one (2.6 g) was added to ethanol (52 ml) which had been saturated with anhydrous ammonia, and the mixture was allowed to stand in a sealed flask at room temperature for three days. The resulting solution was treated with sodiumtetrahydroborate (0.52 g) for two hours, then it was evaporated to low volume, and diluted with water. The product was extracted into 1,1'-oxybisethane, and gaseous hydrogen chloride was passed into the solution, then the precipitate was collected to give 6,7-dihydro-5H-dibenz[b,g]oxocin-6-amine hydrochloride. M.P. 284° C.

EXAMPLE 5

6,7-Dihydro-6-(4-methyl-1-piperazinyl)-5H-dibenz[b,g]oxocine dihydrochloride 5H-Dibenz[b,g]oxocin-6(7H)-one (3 g) was dissolved in a mixture of methylbenzene (30 ml) and N-methylpiperazine (2.25 ml) and the solution was refluxed for sixteen hours, with water being removed via a Dean and Stark trap. The reaction mixture was then evaporated to dryness and the product re-treated, as described above, a further two times. The final residue was triturated with methanol to give 6-(4-methyl-1-piperazinyl)-5H-dibenz[b,g]oxocine. M.P. 127° C.

The enamine (2.7 g - as prepared above) was added to a suspension of 5% Palladium on charcoal (0.27 g) in benzene (54 ml), and the mixture was shaken in an atmosphere of hydrogen, until uptake ceased. The mixture was filtered, and the filtrate was evaporated to dryness. The residue was dissolved in 1,1'-oxybisethane, and gaseous hydrogen chloride was passed into the solution, then the precipitate was collected to give 6,7-dihydro-6-(4-methyl-1-piperazinyl)-5H-dibenz[b,g]-oxocine dihydrochloride. M.P. 273° C. In a similar manner the compound:

3-chloro-6,7-dihydro-6-(4-methyl-1-piperazinyl)-5H-dibenz[b,g]oxocine dihydrochloride was prepared, M.P. 269° C.

We claim:

1. Compound of the formula:

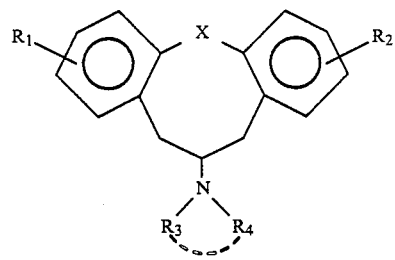

and pharmaceutically acceptable salts thereof, wherein
X represents oxygen, sulphur, NR or —$CH_2$—, in which
R is hydrogen or alkyl (1-4C);
$R_1$ and $R_2$ represent one, two, three or four substituents at the benzo moiety selected from hydrogen, hydroxy, alkyl (1-6C), alkoxy (1-6C), halogen, $CF_3$ and CN; and
$R_3$ and $R_4$, each represent hydrogen or alkyl (1-6C) or together with the nitrogen atom to which they are attached form a heterocyclic 5 or 6-membered ring.

2. Compound according to claim 1, in which X is oxygen.

3. Compound according to claim 1, in which the —$NR_3R_4$ moiety is a N-methylamino or N,N-dimethylamino moiety.

4. Compound according to claim 1, wherein $R_1$ or $R_2$ or both represent a mono- or di-substitution pattern at either of the two benzo moieties.

5. 3-chloro-6,7-dihydro-N-methyl-5H-dibenz[b,g]oxocin-6-amine and pharmaceutically acceptable salts thereof according to claim 1.

6. Pharmaceutical composition comprising an effective amount for antipsychotic activity of the compound of claim 1, together with at least one pharmaceutically acceptable carrier or diluent.

* * * * *